United States Patent [19]

Morelle et al.

[11] 4,089,954
[45] May 16, 1978

[54] METAL SALTS OF FATTY ACID DERIVATIVES OF AMINO ACIDS

[76] Inventors: Jean V. Morelle; Eliane M.-T Lauzanne-Morelle, both of 170 avenue Parmentier, Paris 75010, France

[21] Appl. No.: 621,954

[22] Filed: Oct. 14, 1975

[30] Foreign Application Priority Data

Oct. 28, 1974 France .................... 74 35929

[51] Int. Cl.² ............... A61K 31/555; A61K 31/195; C07F 17/00

[52] U.S. Cl. ................. 424/245; 260/429 R; 260/429.9; 260/438.1; 260/439 R; 260/448 R; 260/518 R; 260/519; 260/534 R; 260/534 C; 260/534 G; 260/534 L; 260/534 M; 260/534 S; 424/287; 424/289; 424/294; 424/295; 424/318; 424/319; 424/320; 424/324

[58] Field of Search ............ 424/319, 289, 287, 294, 424/295, 245, 318, 320, 324; 260/529, 534 R, 534 S, 534 M, 429 R, 429.9, 438.1, 439 R, 448 R, 326.85, 518, 519, 534 C, 534 G, 534 L

[56] References Cited

U.S. PATENT DOCUMENTS

| B 495,781 | 3/1976 | Passedouet et al. | ............ 260/534 R |
|---|---|---|---|
| 3,873,688 | 3/1975 | Kalopissis et al. | ............ 260/534 R |

*Primary Examiner*—Sam Rosen
*Attorney, Agent, or Firm*—Eyre, Mann, Lucas & Just

[57] ABSTRACT

The invention relates to new compositions useful in the field of treatment of man, animals and plants. The compounds are of the formula :

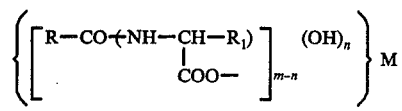

wherein :
R—CO is the acyl moiety of a straight fatty acid RCOOH comprising from 6 to 20 carbon atoms.

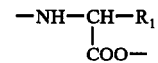

represents either the skeleton of the amino acid

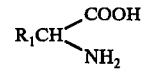

in which $R_1$ is conventionally used to allow the generic designation of any of the naturally occurring α amino acids obtained by degradation of the various proteins, or the ensemble of skeletons of all the α aminoacids obtained by complete hydrolysis of the natural proteins, said compositions containing the alpha aminoacids in proportions similar to that ones existing in the proteins treated.

M is a metal selected from within: magnesium, calcium, iron, cobalt, manganese, copper, zinc, molybdenum and aluminium.

$m$ is the valency of the selected M $n$ is an integer inferior to $m$. Some detailed examples of compositions are given.

2 Claims, No Drawings

METAL SALTS OF FATTY ACID DERIVATIVES OF AMINO ACIDS

This invention relates to new metallic compositions of matter presenting specially an interest in the field of treatment of men, animals and plants.

It is well-known that discrete amounts of metals can be met in all living organisms (human beings, animals, plants) and that they constitute, in all the cases, indispensable elements. The metals are generally encountered under the form of protidic complexes (metalloproteins), glucido protidic or lipido protidic complexes.

These metallic structures play a specific role which varies with the nature of the metal and with the structures of the complexing molecule itself; their action occurs in the field of biocatalysis or in the metabolic exchanges which allow the survival or the growing of the organs or of the organisms.

The major problem lies in the appropriate selection of the complexing structures which must be of such a nature as to allow an acceptable assimilation or absorption by the organ or the organism.

It is well-known that lipoaminoacids and lipopolyaminoacids can easily go through the tissues and cellular membranes due to their specific lipo protidic structures fully compatible with those tissues; although water-insoluble, these lipoaminoacids and lipopolyaminoacids are nevertheless entitled of a certain ionisation capacity which comes from the carboxylic group in alpha position of the amino group; similarly the water insoluble salts of the lipoaminoacids present the same characteristics while bringing together the selected metal.

Accordingly this invention provides the new composition of matter of the formula:

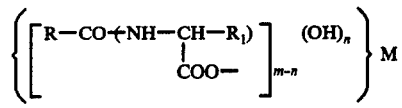

wherein:

R—CO is the acyl moiety of a straight fatty acid RCOOH comprising from 6 to 20 carbon atoms.

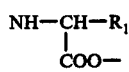

represents either the skeleton of the amino acid

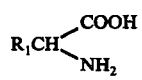

in which $R_1$ is conventionally used to allow the generic designation of any of the naturally occurring α amino acids obtained by degradation of the various proteins, or the ensemble of skeletons of all the α aminoacids obtained by complete hydrolysis of the natural proteins, said compositions containing the alpha aminoacids in proportions similar to that ones existing in the proteins treated.

M is a metal selected from within: magnesium, calcium, iron, cobalt, manganese, copper, zinc, molybdenum and aluminium.

$m$ is the valency of the selected M.

$n$ is an integer inferior to $m$.

The metals retained hereinabove have been specially selected for they are normal constituents of human, animal or vegetable tissues and not toxic to these tissues. Molybdenum and zinc are to be used only in preparations for the treatment of plants whereas all the others are suitable for compositions for the treatment of human and animal tissues.

This invention provides for instance compositions to be used in human and animal therapies for the correction of deficiencies in some of the metals above indicated (preferred forms of administration are creams, ointments and gelatin capsules for instance) and compositions to be used in the treatment of plants which could be presented under the form of aqueous emulsions.

Some examples of formulations are given below:

| | | |
|---|---|---|
| I.- CREAMS FOR TOPICAL USE (proportions in weights) | | |
| A/ | Magnesium palmitoyl collagenate | 5 |
| | Polyethylene cetylic alcohol | 5 |
| | Glycerine | 5 |
| | Stearine | 7 |
| | Isopropylpalmitate | 10 |
| | Conservative agent | 85 |
| | water q.s. | 100 |
| B/ | Magnesium caprylylglycinate | 1 |
| | Polyethylene cetylic alcohol | 1 |
| | Glycerine | 1 |
| | Stearine | 3 |
| | Isopropylpalmitate | 10 |
| | Conservative agent | q.s. |
| | Water q.s. | 100 |
| C/ | Calcium palmitoyl collagenate | 5 |
| | Polyethylene cetylic alcohol | 5 |
| | Glycerine | 5 |
| | Stearine | 7 |
| | Isopropylpalmitate | 10 |
| | Conservative agent | q.s. |
| | Water q.s. | 100 |
| II.- PREPARATIONS FOR ORAL ADMINISTRATION | | |
| A/ | Iron palmitoyl collagenate | 0.250 g |
| | Lactose | 0.050 g |
| | (for a gelatin capsule of 0.3 g) | |
| B/ | Manganese palmitoylglycinate | 0.250 g |
| | Lactose | 0.050 g |
| | (for a gelatin capsule of 0.3 g) | |
| C/ | Cobalt palmitoyl methionate | 0.250 g |
| | Lactose | 0.050 g |
| | (for a gelatin capsule of 0.3 g) | |
| III.- FOR USE IN AGRICULTURE (Proportions in weights) | | |
| | Copper caprylyl methionate | 5 |
| | Polyoxyethylene cetylic alcohol | 10 |
| | Water q.s. | 100 |

These metallic complexes may be prepared either by double decomposition between their soluble salts (alkaline metal salts) and the appropriate metallic soluble salt or by neutralization of the free carboxy group by a base or a metal hydrate. This well-known reactions need no specific description and lead to water insoluble substances which, after precipitation, filtration, washing and drying, give products, the specifications of which are reported in following tables where the compounds are classified by the selected metals.

A-ALUMINIUM SALTS

No. 1-Caprylylglycinate
[CH$_3$—(CH$_2$)$_6$—CO—NH—CH$_2$—COO]$_2$ AlOH    Molecular weight : 444

No. 2-Caprylylcollagenate
[CH$_3$—(CH$_2$)$_6$—CO—(NH—CHR$_1$)] Al (OH)$_2$    M.W. : 307
                              |
                              COO— wherein —(NH—CHR$_1$) represents conventionally the skeletons
              |
              COO—

A-ALUMINIUM SALTS of the ensemble of the aminoacids obtained by the hydrolysis of collagene No. 3-Caprylylcystinate

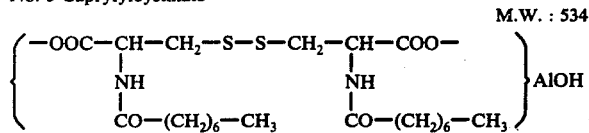
M.W. : 534

No. 4-Caprylylmethionate

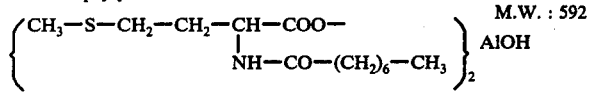
M.W. : 592

No. 5-Palmitoylmethionate

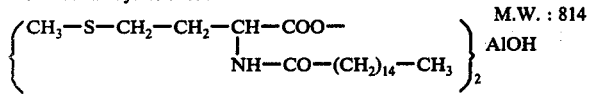
M.W. : 814

A = Theoritical percentage   M.P. = melting point in
B = Found percentage                Celsius degrees

| Ref. No. | % of Metal A | B | M.P. | % of Nitrogen on the lipo aminoacid A | B | on the salt A | B | Aspect |
|---|---|---|---|---|---|---|---|---|
| 1 | 6.1 | 6.5 | 240° | 6.9 | 6.8 | 6.3 | 6.1 | white powder |
| 2 | 8.8 | 9.6 | +300° | 5.7 | 5.4 | 4.5 | 4.2 | " |
| 3 | 6.2 | 7.1 | +300° | 5.7 | 5.4 | 5.2 | 4.8 | " |
| 4 | 4.5 | 4.8 | 184° | 5.1 | 4.7 | 4.6 | 4.3 | " |
| 5 | 3.3 | 3.2 | 66° | 3.6 | 3.2 | 3.4 | 3.1 | " |

B-CALCIUM SALTS

No. 6-Caprylylglycinate
$(CH_3-(CH_2)_6-CO-NH-CH_2-COO)_2 Ca$   M.W. : 442

No. 7-Dipalmitoylhydroxyprolinate

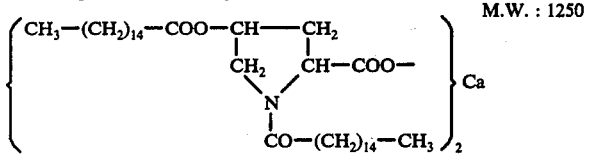
M.W. : 1250

No. 8-Palmitoylcollagenic

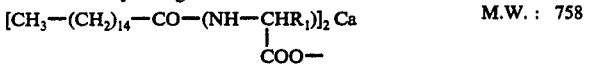
M.W. : 758 please refer to compound number 2 for the understanding of $-(NH-CHR_1)$
$\phantom{xxxxxxxxxxxxxxxxxxx}|$
$\phantom{xxxxxxxxxxxxxxxxxxx}COO-$ No. 9-Palmitoylcaseinic

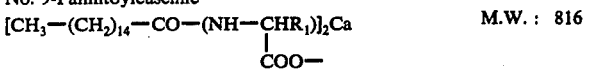
M.W. : 816 definition of $-(NH-CHR_1)$ comparable to compound 2
$\phantom{xxxxxxxxxxxx}|$
$\phantom{xxxxxxxxxxxx}COO-$
except that collagene is replaced by caseine No. 10-Caprylylcollagenate

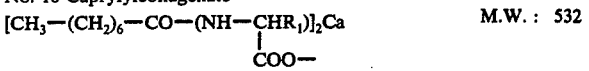
M.W. : 532

Same definition as in compound 8.
No. 11-Caprylylcystinate

B-CALCIUM SALTS

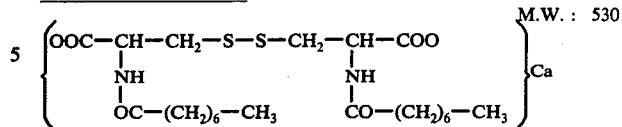
M.W. : 530

No. 12-Lauroylcollagenate

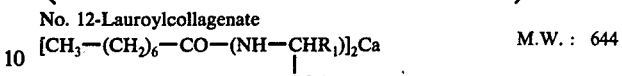
M.W. : 644

Same definition as in compound 8.

A = Theoritical percentage   M.P. = melting point in
B = Found percentage                Celsius degrees

| Ref. No. | % of metal A | B | M.P. | % of Nitrogen on the lipo aminoacid A | B | on the salt A | B | Aspect |
|---|---|---|---|---|---|---|---|---|
| No. 6 | 9.1 | 8.4 | 250° | 6.9 | 6.8 | 6.3 | 5.9 | white powder |
| No. 7 | 3.2 | 3.6 | 155° | 2.3 | 2.1 | 2.2 | 2.1 | " |
| No. 8 | 5.3 | 4.9 | 170° | 3.9 | 3.6 | 3.7 | 3.5 | " |
| No. 9 | 4.9 | 3.8 | 145° | 3.6 | 3.1 | 3.4 | 2.9 | " |
| No. 10 | 7.5 | 6.8 | 172° | 5.7 | 5.4 | 5.2 | 4.9 | " |
| No. 11 | 7.5 | 8.4 | +250° | 5.7 | 5.4 | 5.2 | 4.7 | " |
| No. 12 | 6.2 | 5.4 | 105° | 4.6 | 4.3 | 4.3 | 4.1 | " |

C-COBALT SALTS

No. 13-Palmitoylcollagenate

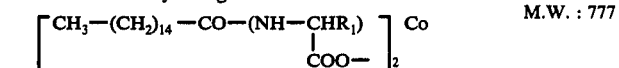
M.W. : 777 same definition as in example 2

No. 14-Palmitoylmethionate

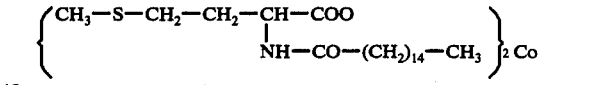
M.W. : 833

No. 15-Caprylylcystinate

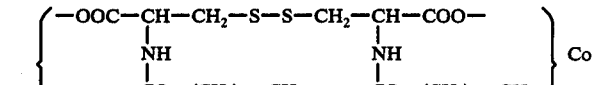
M.W. : 551

No. 16 -Undecylenoylglycinate
$(CH_2=CH-(CH_2)_8-CO-NH-CH_2-COO)_2 Co$   M.W. : 539
No. 17-Lauroylglycinate
$(CH_3-(CH_2)_6-CO-NH-CH_2-COO)_2 Co$   M.W. : 571

A = Theoritical percentage   M.P. = melting point in
B = Found percentage                Celsius degrees

| Ref. No. | % of metal A | B | M.P. | % of Nitrogen on the lipo aminoacid A | B | on the salt A | B | Aspect |
|---|---|---|---|---|---|---|---|---|
| No. 13 | 7.6 | 8.2 | 105° | 3.9 | 3.6 | 3.6 | 3.2 | violet pink powder |
| No. 14 | 7.1 | 7.8 | 123° | 3.6 | 3.2 | 3.3 | 3.1 | " |
| No. 15 | 10.7 | 11.5 | 240° | 5.7 | 5.2 | 5.1 | 4.9 | " |
| No. 16 | 10.9 | 9.2 | 168° | 5.8 | 5.4 | 5.2 | 4.7 | " |
| No. 17 | 10.3 | 9.3 | 145° | 5.4 | 4.8 | 4.4 | 4.1 | " |

D-COPPER SALTS

No. 18-Caprylylglycinat
$(CH_3-(CH_2)_6-CO-NH-CH_2-COO)_2 Cu$   M.W. : 463
No. 19-Caprylylmethionate

D-COPPER SALTS

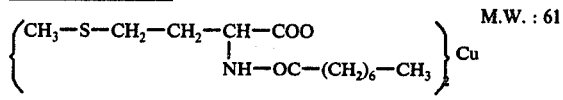  M.W.: 611

No. 20-Palmitoylcollagenate

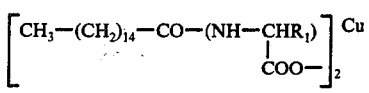  M.W.: 781 please refer to compound number 2 for the understanding of —(NH—CHR₁)
                                                                |
                                                               COO—

No. 21-Palmitoylkeratinic

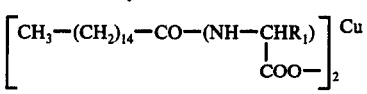  M.W.: 821

Definition comparable to compound 20 except that collagene is replaced by keratine No. 22-Caprylylcollagenate

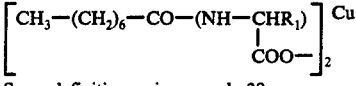  M.W.: 555

Same definition as in example 20

No. 23-Lauroylcollagenate

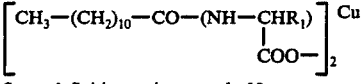  M.W.: 669

Same definition as in example 20

No. 24-Oleyl collagenate of copper  M.W.: 829

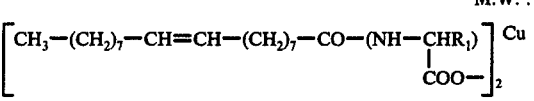

Same definition as in example 20

| | | | % of Nitrogen | | | | |
|---|---|---|---|---|---|---|---|
| A = Theoretical percentage | | | | | M.P. : melting point in Celsius degrees | | |
| B = Found percentage | | | | | | | |
| | | | on the lipo aminoacid | | on the salt | | |
| Ref. No. | % of metal | | M.P. | | | | Aspect |
| | A | B | | A | B | A | B | |
| No. 18 | 13.5 | 11.8 | 170° | 6.9 | 6.7 | 6 | 5.7 | green powder |
| No. 19 | 10.3 | 9.7 | 180° | 5.1 | 4.7 | 4.6 | 4.3 | " |
| No. 20 | 8.1 | 7.3 | 85° | 3.7 | 3.5 | 3.6 | 3.2 | " |
| No. 21 | 7.7 | 6.9 | 80° | 3.7 | 3.4 | 3.4 | 3.1 | " |
| No. 22 | 11.4 | 9.8 | 145° | 5.7 | 5.4 | 5.0 | 4.7 | " |
| No. 23 | 9.5 | 8.6 | 90° | 4.6 | 4.3 | 4.2 | 3.8 | " |
| No. 24 | 7.6 | 6.9 | 55° | 8.1 | 7.4 | 3.1 | 2.8 | " |

E-IRON SALTS

No. 25-Palmitoylcollagenate  M.W.: 774

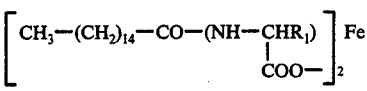

please refer to compound number 2 for the understanding of —(NH—CHR₁)
                                                                |
                                                               COO—

No. 26-Caprylylcollagenate  M.W. 550

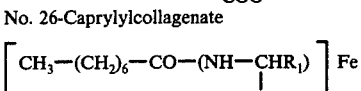

same definition as in example 25

F-ZINC SALTS

No. 27-Caprylylglycinate

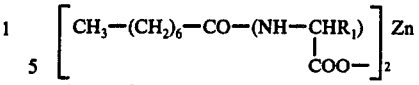  M.W.: 465 please refer to compound 2 for the understanding of

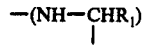

G-MANGANESE SALTS

No. 28-Palmitoylcollagenate

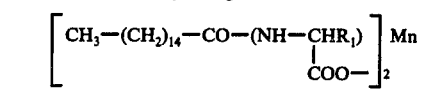  M.W.: 773 please refer to compound 2 for the understanding of

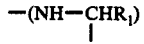

No. 29-Caprylylglycinate

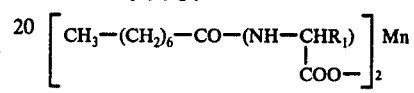  M.W. 455

Same definition as in example 28

| | | | % of Nitrogen | | | | |
|---|---|---|---|---|---|---|---|
| A = Theoritical percentage | | | | | M.P. = melting point in Celsius degrees | | |
| B = Found percentage | | | | | | | |
| | | | on the lipo aminoacid | | on the salt | | |
| Ref. No. | % of Metal | | M.P. | | | | Aspect |
| | A | B | | A | B | A | B | |
| No. 25 | 7.23 | 6.46 | 90° | 3.9 | 3.6 | 3.6 | 3.2 | red ochre powder |
| No. 26 | 10.1 | 9.2 | 130° | 5.7 | 5.4 | 5.1 | 4.6 | " |
| No. 27 | 13.9 | 12.8 | >200° | 7.0 | 6.2 | 6.0 | 5.1 | white powder |
| No. 28 | 7.1 | 6.7 | 97° | 3.9 | 3.6 | 3.6 | 3.2 | beige powder |
| No. 29 | 12 | 13.2 | 199° | 6.9 | 6.8 | 6.1 | 5.8 | " |

H-MAGNESIUM SALTS

No. 30-Palmitoylcollagenate

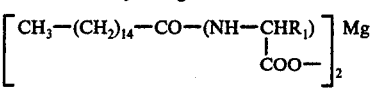  M.W.: 742 please refer to compound number 2 for the understanding of —(NH—CHR₁)
                                                                |
                                                               COO—

No. 31-Caprylylcollagenate

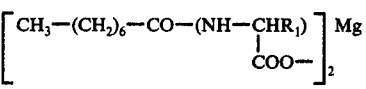  M.W.: 518 same definition as in example 30

No. 32-Palmitoylmethionate

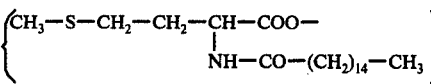  M.W.: 796

No. 33-Caprylylmethionate

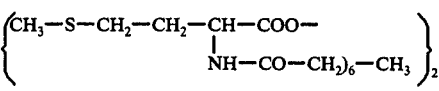  M.W.: 572

No. 34-Caprylylglycinate
(CH₃—(CH₂)₆—CO—NH—CH₂—COO)₂ Mg   M.W.: 424

No. 35-Lauroylaspartate

-continued

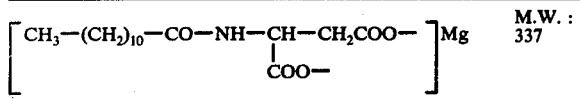 M.W.: 337

No. 36-Caproylglycinate
$(CH_3-(CH_2)_4-CO-NH-CH_2-COO)_2$ Mg  M.W.: 368

| | | | | % of Nitrogen | | | | |
|---|---|---|---|---|---|---|---|---|
| A = Theoritical percentage | | | | M.P. = melting point in Celsius degrees | | | | |
| B = Found percentage | | | | | | | | |
| Ref. | % of Metal | | | on the lipo aminoacid | | on the salt | | |
| No. | A | B | M.P. | A | B | A | B | Aspect |
| No. 30 | 3.2 | 2.6 | 99° | 3.9 | 3.6 | 3.8 | 3.4 | White powder |
| No. 31 | 4.6 | 4.2 | 185° | 5.7 | 5.4 | 5.4 | 4.8 | " |
| No. 32 | 3.0 | 2.7 | 157° | 3.6 | 3.3 | 3.5 | 3.2 | " |
| No. 33 | 4.2 | 3.8 | 200° | 5.1 | 4.7 | 4.9 | 4.7 | " |
| No. 34 | 5.6 | 5.2 | 185° | 6.9 | 6.8 | 6.6 | 6.2 | " |
| No. 35 | 7.1 | 7.8 | >200° | 4.4 | 4.1 | 4.1 | 3.8 | " |
| No. 36 | 6.5 | 5.9 | >200° | 8.1 | 7.4 | 7.6 | 7.1 | " |

The compositions according to this invention may be used, for instance:

for those containing calcium salts, for the treatment of affections in relationship with the teeth and the bones;

for those containing aluminium salts in hygienic preparations acting against the sudation;

for those containing cobalt salts, as hemato poietic factors;

for those containing manganese and magnesium salts, as growing factors more particularly for cattle;

for those containing copper salts, as biosynthetic (synthesis of cuproproteins) and in the treatment of cryptogamic diseases.

We claim:

1. A compound of the formula

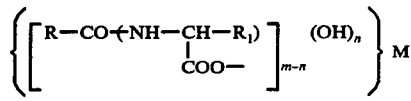

wherein:
(a) R—CO is the acyl moiety of a straight fatty acid RCOOH comprising from 6 to 20 carbon atoms;
(b)

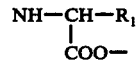

represents the skeleton of the amino acid

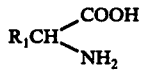

in which $R_1$ is conventionally used to allow the generic designation of any of the naturally occurring amino acids obtained by degradation of the various proteins;
(c) M is a metal selected from the group consisting of magnesium, calcium, iron, cobalt, manganese, copper, zinc, molybdenum and aluminium;
(d) m is the valency of the selected M; and
(e) n is an integer inferior to m.

2. A therapeutic composition for the treatment of deficiencies in metal in living organisms, said therapeutic composition comprising a carrier and an effective amount of an active ingredient which is at least one compound selected from those of claim 1.

* * * * *

UNITED STATES PATENT AND TRADEMARK OFFICE
CERTIFICATE OF CORRECTION

PATENT NO. : 4,089,954
DATED : May 16, 1978
INVENTOR(S) : Jean V. Morelle: Eliane M.T. Lauzanne-Morelle It is certified that error appears in the above-identified patent and that said Letters Patent are hereby corrected as shown below:

Column 1, line 52, "either" should be underlined.

Column 1, line 61, "or" should be underlined.

Column 2, 1st Chart, line 6 of A/, "85" should read --q.s.--.

Column 2, 1st Chart, line 1, 2, and 3 of B/, "1" should read --5--.

Column 2, 1st Chart, line 4 of B/, "3" should read --7--.

Column 3, line 61, "2" should read --8--.

Signed and Sealed this

Nineteenth Day of September 1978

[SEAL]

Attest:

RUTH C. MASON
Attesting Officer

DONALD W. BANNER
Commissioner of Patents and Trademarks